United States Patent
Knüppel et al.

(10) Patent No.: US 6,204,397 B1
(45) Date of Patent: *Mar. 20, 2001

(54) PROCESS FOR THE PREPARATION OF 3-SUBSTITUTED 4-CYANO-PYRROLE COMPOUNDS

(75) Inventors: Peter C. Knüppel, Wermelskirchen; Reinhard Lantzsch; Klaus Jelich, both of Wuppertal; Peter Andres, Leichlingen; Albrecht Marhold, Leverkusen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 08/086,602

(22) Filed: Jul. 1, 1993

Related U.S. Application Data

(62) Division of application No. 07/843,480, filed on Feb. 28, 1992, now Pat. No. 5,258,526.

(30) Foreign Application Priority Data

Mar. 8, 1991 (DE) .................................... 41 97 398

(51) Int. Cl.⁷ ............................................... C07D 317/52
(52) U.S. Cl. ............................................................ 549/434
(58) Field of Search .............................................. 549/434

(56) References Cited

U.S. PATENT DOCUMENTS

| | | | |
|---|---|---|---|
| 2,727,896 | * 12/1955 | Yale et al. | 548/517 |
| 4,564,479 | 1/1986 | Spencer | 260/465 H |
| 4,820,835 | 4/1989 | Burger | 540/577 |
| 4,912,229 | 3/1990 | Wollweber | 548/532 |
| 4,923,994 | 5/1990 | Wollweber | 546/281 |
| 4,958,030 | 9/1990 | Pflunger | 548/526 |
| 4,960,789 | 10/1990 | Wollweber | 514/427 |
| 4,965,363 | 10/1990 | Wollweber | 548/561 |
| 5,015,757 | 5/1991 | Wollweber | 558/401 |
| 5,091,408 | * 2/1992 | Wollweber et al. | 514/427 |
| 5,281,725 | * 1/1994 | Andres et al. | 549/439 |

FOREIGN PATENT DOCUMENTS

| | | |
|---|---|---|
| 2927480 | 7/1979 | (DE) . |
| 3642256 | * 6/1987 | (DE) . |
| 3800387 | 1/1988 | (DE) . |
| 0061907 | 10/1982 | (EP) . |
| 0078768 | 10/1982 | (EP) . |
| 0174910 | 3/1986 | (EP) . |
| 0206999 | 6/1986 | (EP) . |
| 0318704 | 10/1988 | (EP) . |
| 0310558 | 4/1989 | (EP) . |
| 0333661 | 9/1989 | (EP) . |
| 0378046 | 12/1989 | (EP) . |

OTHER PUBLICATIONS

Houben–Weyl, *Methoden der Organischen Chemie,* 1960, p. 441.
Tetrahedron Lett. 52, 5337 (1972).
Tetrahedron Lett. 41, 1259 (1985).
J. Amer. Chem. Soc. 83, 1833 (1961).
Tetrahedron Lett 43, 587 (1987).
Abstract of JP 60 38 336, Aug, 12, 1983.
J. Org. Chem 34, 714 (1969).
J. Organomet. Chem. 258, 101 (1983).
Tetrahedron Lett. 1972, 2363–2368.
Angew. Chem. 83, 357–358 (1971).
Angew. Chem. 86, 878ff (1974).
Lei Bigs Ann Chem, 615, 124 (1958).
Chemical Abstract, 27–Heterocycles, vol. 111, 1989, p. 703.
Chemical Abstract, 28–Heterocycles, vol. 112, 1990, p. 719.

* cited by examiner

*Primary Examiner*—Ba K. Trinh
(74) *Attorney, Agent, or Firm*—Norris McLaughlin & Marcus

(57) ABSTRACT

A process for the preparation of 3-substituted 4-cyano-pyrrole compounds of the formula (I)

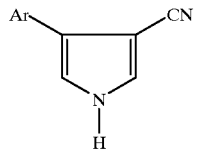

in which
Ar has the meaning given in the description, by reaction in a 1st stage of bromides (II)

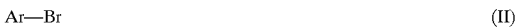

Ar—Br          (II)

with acrylonitrile in the presence of a solvent and a suitable reaction auxiliary to give acrylonitrile derivatives (III)

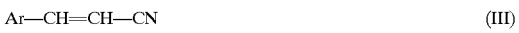

Ar—CH=CH—CN          (III)

and in a 2nd stage with a phenylsulphonylmethyl isocyanide (IV)

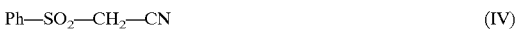

Ph—SO₂—CH₂—CN          (IV)

in the presence of a solvent and optionally in the presence of a suitable reaction auxiliary, characterised in that the the 1st stage is carried out in the presence of a palladium catalyst and the 2nd stage in the presence of a 1.2- to 1.8-fold molar excess of alkali metal alcoholate or alkali metal hydroxide.

1 Claim, No Drawings

PROCESS FOR THE PREPARATION OF 3-SUBSTITUTED 4-CYANO-PYRROLE COMPOUNDS

This is a division, of U.S. application Ser. No. 07/843,480, filed Feb. 28, 1992, now U.S. Pat. No. 5,258,526.

The invention relates to a new process for the preparation of 3-substituted 4-cyano-pyrrole compounds which may be used as pesticides.

It is known that fungicidally active 3-aryl-4-cyano-pyrrole compounds are obtainable when the correspondingly substituted cinnamonitriles are reacted with p-toluenesulphonylmethyl isocyanide (TOSMIC) in the presence of sodium hydride (compare DE-OS (German Published Specification) 29 27 480 or Tetrahedron Lett. 52, 5337 [1972]). However, this process with yields of approximately 35–45% only gives unsatisfactory results. Also it is disadvantageous that the compounds thus obtainable must be laboriously purified (compare JP 61 30 571). Finally, both the reagents sodium hydride and p-toluenesulphonylmethyl isocyanide (TOSMIC) are not very well suited for technical syntheses, the first because of the high susceptibility to hydrolysis, and the associated fire risk from the gaseous hydrogen liberated during hydrolysis, and the second because of the easy decomposability at elevated temperature (compare EP 174 910).

No better suited for industrial syntheses is the n-butyllithium used as base in an analogous process (compare EP 333 661), which is also very susceptible to hydrolysis and is moreover laborious and expensive to prepare. The use of other bases is described, but with these also only unsatisfactory conversions are achieved (compare e.g. EP 310 558 or EP 206 999).

It is further known that the cinnamonitriles required for the synthesis of 3-aryl-4-cyano-pyrrole compounds are obtained by processes disclosed in the literature, as for example by a WITTIG reaction (compare e.g. Tetrahedron 41, 1259 [1985] or J. Amer. Chem. Soc. 83, 1733 [1961] or Synthesis 1977, 126) or by the KNOEVENAGEL condensation (compare e.g. Tetrahedron 43, 537 [1987] or Tetrahedron Lett. 1979, 553 or EP 378 046) from benzaldehydes. However, the synthesis of the benzaldehydes required for this is extraordinarily difficult, laborious and proceeds via many stages (compare e.g. EP 61 907 or JP 60 38 336 or EP 333 658).

The large-scale preparation of the 3-substituted 4-cyano-pyrrole compounds desired as fungicidally active end products via the literature-disclosed route of the α-substituted cinnamonitriles (compare e.g. DE-OS (German Published Specification) 37 18 375 or DE-OS (German Published Specification) 38 00 387 or EP 324 336 or EP 378 046) fails finally because first these benzaldehydes, which are very difficult to synthesise, are required as starting compounds.

The alternative preparation of the cinnamonitriles required as precursors, from corresponding aromatic amines by MEERWEIN arylation gives very poor yields, particularly in the case of the desired 2,3-disubstituted aryl compound (compare EP 318 704 or EP 206 999 or J. Org. Chem 34, 714 [1969]).

Finally it is known that the cinnamonitriles required as precursors may also be obtained when bromides or iodides are reacted with acrylonitrile in the presence of a palladium catalyst and a phosphine as reaction auxiliary in basic or dipolar-aprotic solvents such as for example triethylamine or dimethylformamide (compare e.g. EP 78 768 or U.S. Pat. No. 4,820,835 or J. Chem. Soc., Perkin Trans. 1, 2597 [1987] or J. Organomet. Chem. 258, 101, [1983]). However, this reaction also fails in the case of the 2,3-disubstituted aryl compounds. Under the reaction conditions disclosed in the literature only a low conversion to the desired end product was achieved (compare the Preparation Example III-1).

It has now been found that the 3-substituted 4-cyano-pyrrole compounds of the general formula (I),

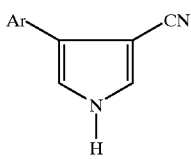

in which
Ar represents an at least 2,3-disubstituted aryl radical or substituted heteroaryl radical,
are obtained by reaction of bromides of the formula (II), $$Ar—Br \qquad (II)$$

in which
Ar has the meaning given above,
in a first stage with acrylonitrile in the presence of a suitable solvent and a suitable reaction auxiliary, and of the aryl-acrylonitrile derivatives thus obtainable of the formula (III), $$Ar—CH=CH—CN \qquad (III)$$

in which
Ar has the meaning given above,
in a second stage with phenylsulphonylmethyl isocyanides of the formula (IV), $$Ph—SO_2—CH_2—NC \qquad (IV)$$

in which
Ph represents optionally substituted phenyl,
in the presence of a suitable diluent and optionally in the presence of a suitable reaction auxiliary, in especially favourable manner, particularly in high purity and high yield, by a process which is characterised in that the first stage is carried out in the presence of a palladium catalyst and the second stage in the presence of a 1.2- to 1.8-fold molar excess of alkali metal alcoholate or alkali metal hydroxide as base to give the acrylonitrile derivative.

Surprisingly, in the process according to the invention, the conversion of the acrylonitrile derivatives of the formula (III) with phenylsulphonyl-methyl isocyanides of formula (IV) in the second stage in the presence of a 1.2- to 1.8-fold molar excess of alkali metal alcoholate or alkali metal hydroxide as base succeeds in very high yields, although it was known from the prior art that weaker bases than sodium hydride, that is including alkali metal alcoholates or alkali metal hydroxides, give only poor yields (compare e.g. EP 310 558 or EP 206 999).

The use of an excess of base was also countered by the assumption that such an excess of base in the reaction mixture could react with the starting materials used as well as with the end product and that these side reactions would lead to undesired by-products and to a marked reduction in yield of the desired end product. (For side reactions of base and Tosmic compare e.g. Tetrahedron Lett. 1972, 2363–2368; Angew. Chem. 83, 357–358 [1971]; Angew.

Chem. 86, 878ff [1974]; for side reactions of base and acrylonitrile in the presence of pyrrole, compare e.g. Liebigs Ann. Chem. 615, 124 [1958]; J. Chem. Soc. 1962, 4346.)

Further, it is surprising that the conversion of the bromides of formula (II) with acrylonitrile in the presence of palladium in the first stage of the process according to the invention, without the literature described addition of phosphines, as reaction auxiliaries, gives very high yields, especially as the reaction conditions described in the literature (compare e.g. EP 78 768 or U.S. Pat No. 4,820,835 or J. Chem. Soc., Perkin Trans 1, 1987 2597 or J. Organomet. Chem. 258, 101, [1983]) fail in the case of aryl compounds at least 2,3-disubstituted in the aryl part, which are of particular interest as fungicides; under the conditions described in the literature, almost no reaction occurs.

The process according to the invention has a number of advantages over the previously known processes:

For example, avoidance of phosphines as reaction auxiliaries in the first stage means that there are considerably fewer effluent problems, since phosphines and their reaction products—including in particular phosphine oxides—may be removed only with difficulty from the resulting effluent on account of their high water solubility.

A further advantage is the avoidance in the second stage of sodium hydride, which is difficult to handle industrially and requires complicated safety precautions. The alkali metal alcoholates or alkali metal hydroxides used as bases in the process according to the invention are cheap to prepare, simple to handle and harmless from the safety aspect.

It was further known from the prior art that the phenylsulphonylmethyl isocyanide may be replaced by substituted phenylsulphonylmethyl isocyanides such as 4-chlorophenyl- or 4-methylphenylsulphonylmethyl isocyanide. However, it was not previously known that the substituted compounds bring additional advantages. Thus the 4-chlorophenyl compound displays a low thermo—lability, which widens the safety margins, and can be used more economically with respect to its preparation and recovery from its reaction end products (sodium or potassium p-chlorophenylsulphinate). The 4-methylphenyl compound is also usable here, since the 2nd stage of the process according to the invention gives very high yields even at low reaction temperatures, and the temperature region where the thermal lability of the p-toluenesulphonylmethyl isocyanide begins to become problematical is not reached.

The last but not least important advantage of the process according to the invention lies in a considerable increase in total yield of the fungicidal end product in comparison with the previously known processes.

The 3-substituted 4-cyano-pyrrole compounds obtainable with the aid of the process according to the invention are defined in general terms by the formula (I). Preferably preparable are compounds of the formula (I) in which Ar represents an at least 2,3-disubstituted aryl radical having 6 or 10 carbon atoms, such as phenyl and naphthyl, or a mono- to pentasubstituted mononuclear or polynuclear heteroaryl radical having 2 to 9 carbon atoms and 1 to 4 heteroatoms, especially oxygen, sulphur and/or nitrogen, such as e.g. pyridyl, thienyl, furyl, benzodioxolyl, benzodioxanyl, where the substituents are identical or different and possible substituents in each case are: halogen, cyano, nitro, alkyl, alkoxy or akylthio each of which may be straight-chain or branched, each having 1 to 4 carbon atoms, halogenoalkyl, halogenoalkoxy or halogenoalkylthio each of which may be straight-chain or branched, each having 1 to 4 carbon atoms and 1 to 9 identical or different halogen atoms, alkoxycarbonyl or alkoximinoalkyl each of which may be straight-chain or branched, each having 1 to 4 carbon atoms in the individual alkyl moieties.

Especially preferably preparable are compounds of the formula (I) in which

Ar represents an at least 2,3-disubstituted phenyl radical, or a mono- to trisubstituted mononuclear or binuclear 5-membered or 6-membered heteroaryl radical having 2 to 8 carbon atoms and 1 to 3 heteroatoms, especially nitrogen, oxygen and/or sulphur, where possible identical or different substituents in each case are: fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl or ethoximinoethyl.

Very especially preferably preparable are compounds of the formula (I) in which

Ar represents an identically or differently at least 2,3-disubstituted phenyl radical or a mono-, di- or trisubstituted 2-pyridyl radical, 4-pyridyl radical, 2-furyl radical, 2-thienyl radical, benzodioxolyl or benzodioxolanyl, where possible substituents in each case are: fluorine, chlorine, bromine, methyl, ethyl, methoxy, ethoxy, methylthio, trifluoromethyl, trifluoromethoxy, trifluoromethylthio, nitro or cyano.

Particularly preferably preparable are compounds of the formula (I) in which

Ar represents 2,3-dichlorophenyl, 2,3-difluorophenyl, 2-fluoro-3-chlorophenyl, 2-chloro-3-fluorophenyl, 2,4-difluoro-3-chlorophenyl, 2-fluoro-3-trifluoromethylphenyl or 2,2-difluorobenzodioxolyl.

If for example 1-bromo-2-fluoro-3-chlorophenyl is used as the starting compound, then the course of the reaction in the process according to the invention can be represented by the following formula equation:

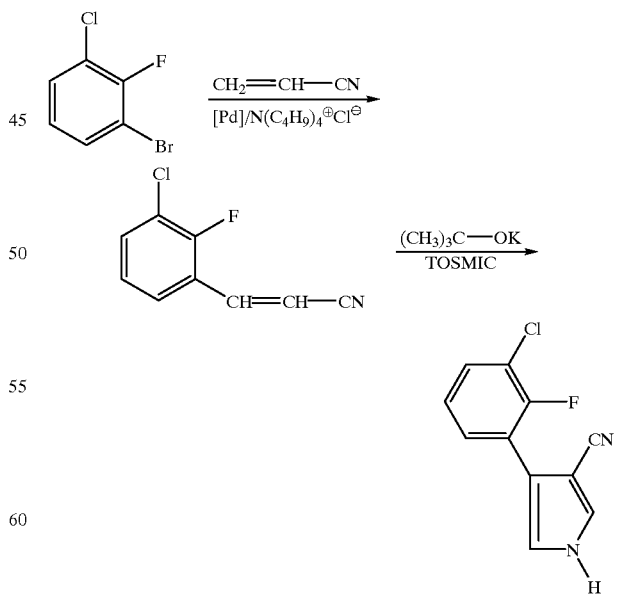

Only some of the bromides of the formula (II) required as starting substances for carrying out the process according to the invention are known (compare e.g. J. Chem. Perkin Trans. 2, 1972, 1733 or J. Chem. Soc. 79, 1302 [1901] J. Amer. Chem. Soc. 87, 2640 [1965] or Org. Magn. Reson. 9, 155 [1977] or Circ. Ill. State Geol. Surv. 1979, 508 (17 ff.) or CA 92:53358d).

Compounds of the formula (IIa)

in which
Ar$^1$ represents 2-fluoro-3-chlorophenyl, 2-fluoro-3-trifluoromethylphenyl or 2,2-difluorobenzodioxolyl, are new.

Compounds of the formula (IIa) are also a subject of the invention.

The new and known bromides of the formulae (II) or (IIa) are obtained when amines of the formula (V)

or

in which
Ar and Ar$^1$ have the meaning given,
are reacted with sodium nitrite in the presence of, for example, hydrobromic acid and in the presence of a catalyst.

Alternatively it is also possible to prepare the compounds of the formula (IIb),

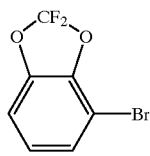

by reacting 2,2-difluorobenzodioxole (compare e.g. DE 19 21 741) firstly with n-butyllithium in the presence of a diluent such as, for example, tetrahydrofuran at temperatures between −80° C. and −60° C., then adding elemental bromine, hydrolysing the product in a conventional manner with dilute hydrochloric acid at room temperature, and working up by known methods (compare for example EP 333 658 or the preparation examples for this).

The phenylsulphonylmethyl isocyanides needed as starting compounds for carrying out the second stage of the process according to the invention are defined in general terms by the formula (IV). In this formula (IV) Ph represents preferably optionally mono- or disubstituted, identically or differently substituted phenyl: where possible substituents are: fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, trifluoromethylthio, methoxycarbonyl or ethoxycarbonyl. Ph represents in particular optionally monosubstituted phenyl, where possible substituents are: fluorine, chlorine, bromine, cyano, nitro, methyl, ethyl, n- or i-propyl, n-, i-, s- or t-butyl, methoxy, ethoxy, n- or i-propoxy. Very especially preferred radicals for the Ph substituents are the 4-methylphenyl radical and the 4-chlorophenyl radical.

Phenylsulphonylmethyl isocyanides of the formula (V) are known or are obtainable with the aid of known processes (compare e.g. DE-OS (German Published Specification) 36 01 285 or U.S. Pat. No. 4.680.413 or Tetrahedron Lett. 1972, 2367 or J. Org. Chem. 42, 1153 [1977] or Synthesis 1985, 400 or Organic Syntheses 57, 102 [1977]).

The diluent for preparation of the starting bromides of the formula (II) can be all diluents conventional for such diazotisation reactions. Preferably, aqueous systems are used, in particular aqueous protonic acids, such as for example sulphuric acid, nitric acid, hydrochloric acid or hydrobromic acid.

The process for preparation of the bromides (II) is carried out in the presence of a suitable catalyst. These can be with special preference copper-(I) salts, such as for example copper-(I) chloride, copper-(I) iodide and in particular copper-(I) bromide.

The reaction temperatures can be varied in a wide range. In general temperatures between −20° C. and +120° C. are used, preferably temperatures between +5° C. and +90° C.

For carrying out the process for the preparation of the starting product, in general 1.0 to 5.0 mol, preferably 1.0 to 2.5 mol, of sodium nitrite, 1.0 to 10.0 mol, preferably 1.0 to 5.0 mol, of highly concentrated hydrobromic acid and 0.01 to 1.0 mol, preferably 0.05 to 0.5 mol, of copper-(I) catalyst are used per mole of the amine of the formula (V). The reaction is carried out in analogy to known standard processes (compare e.g. HoubenWeyl "Methoden der organischen Chemie" Volume V,1 p.441 or Organic Syntheses Coll. Vol. III, 185 [1955]). In order to avoid side reactions, the reaction temperature should only exceed 40° C. for a short time. The work-up and isolation of the reaction products proceeds according to conventional, generally known methods (compare also the preparation examples).

The first stage of the process according to the invention is carried out in the presence of a suitable palladium catalyst. Palladium salts are possible for this, such as for example palladium chloride, palladium acetate or palladium sulphate or elemental palladium, optionally on a suitable support such as for example activated charcoal or silicon dioxide.

Possible diluents for carrying out the first stage of the process according to the invention are inert organic solvents. These include in particular aliphatic, alicyclic or aromatic, optionally halogenated hydrocarbons, such as for example benzine, benzene, toluene, xylene, chlorobenzene, dichlorobenzene, petroleum ether, hexane, cyclohexane, carbon tetrachloride; ethers,such as diethyl ether, diisopropyl ether, dioxane, tetrahydrofuran, ethylene glycol dimethyl ether or ethylene glycol diethyl ether or diethylene glycol dimethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoric acid triamide; esters, such as methyl acetate or ethyl acetate; sulphoxides, such as dimethyl sulphoxide or alcohols, such as methanol, ethanol, n- ori-propanol, n-butanol, i- butanol, s-butanol, ethylene glycol monomethyl ether or ethylene glycol monoethyl ether.

Aprotic polar solvents, such as tetrahydrofuran, dioxane, ethylene glycol dimethyl ether and ethylene glycol diethyl ether, diethylene glycol dimethyl ether, dimethylformamide, dimethylacetamide and N-methylpyrrolidone are particularly preferred diluents for carrying out the first stage of the process according to the invention.

The first stage of the process according to the invention is carried out in the presence of a suitable reaction auxiliary. For this all usual inorganic or organic bases are possible. These include for example alkaline earth or alkali metal hydroxides such as sodium hydroxide, calcium hydroxide, potassium hydroxide or also ammonium hydroxide, alkyli metal carbonates, such as sodium carbonate, potassium carbonate, potassium hydrogen carbonate, sodium hydrogen carbonate or ammonium carbonate, alkali or alkaline earth metal acetates, such as sodium acetate, potassium acetate, calcium acetate or ammonium acetate, as well as tertiary amines, such as trimethylamine, triethylamine, tributylamine, N,N-dimethylaniline, pyridine, piperidine, N-methylpiperidine, N,N-dimethylaminopyridine, diazabicyclooctane (DABCO), diazabicyclononene (DBN) or diazabicycloundecene (DBU).

Moreover, it is advantageous to add a suitable phase transfer catalyst as a further reaction auxiliary. Examples of such catalysts which may be mentioned are: tetrabutylammonium iodide, tetrabutylammonium bromide, tetrabutylammonium chloride, tributyl-methylphosphonium bromide, trimethyl-$C_{13}/C_{15}$-alkylammonium chloride, trimethyl-$C_{13}/C_{15}$-alkylammonium bromide, dibenzyl-dimethylammonium methylsulphate, dimethyl-$C_{12}/C_{14}$-alkyl-benzylammonium chloride, dimethyl-$C_{12}/C_{14}$-alkyl-benzylammonium bromide, tetrabutylammonium hydroxide, triethylbenzylammonium chloride, methyltrioctylammonium chloride, trimethylbenzylammonium chloride, 15-crown-5, 18-crown-6 or tris-[2-(2-methoxyethoxy)-ethyl]-amine.

The reaction temperatures may be varied in the first stage of the process according to the invention in a wide range. In general temperatures between 50° C. and 250° C. are used, preferably temperatures between 100° C. and 150° C.

The process according to the invention is in general carried out at standard pressure. However, it is also possible to work at reduced or increased pressure. Possible pressure ranges are between 0.5 and 100 bar, preferably between 0.9 and 10 bar.

To carry out the first stage of the process according to the invention, in general 1.0 to 5.0 mol, preferably 1.0 to 2.0 mol, of acrylonitrile, 0.1 to 0.0001 mol, preferably 0.01 to 0.001 mol, of palladium catalyst, optionally 1.0 to 5.0 mol, preferably 1.0 to 2.5 mol, of the base used as reaction auxiliary and optionally 0.01 to 2.0 mol, preferably 0.1 to 1.5 mol, of a phase transfer catalyst are used per mole of the bromide of the formula (II). The reaction procedure, work-up and isolation of the reaction products are achieved according to known processes (compare in this respect the preparation examples).

Possible diluents for carrying out the second stage of the process according to the invention are inert organic solvents. These include in particular aliphatic, alicyclic or aromatic, optionally halogenated hydrocarbons, such as for example benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, methyl tert-butyl ether, dioxane, tetrahydrofuran, or ethylene glycol dimethyl ether or ethylene glycol diethyl ether; nitriles, such as acetonitrile, propionitrile or benzonitrile; amides, such as N,N-dimethylformamide, N,N-dimethylacetamide, N-methylformanilide, N-methylpyrrolidone or hexamethylphosphoric acid triamide; esters, such as methyl acetate, ethyl acetate; alcohols, such as methanol, ethanol, n- or i-propanol, ethylene glycol monomethyl ether or ethylene glycol monoethyl ether.

The second stage of the process according to the invention is carried out in the presence of a suitable base. Alkali metal alcoholates or alkali metal hydroxides have proven to be particularly suitable, such as for example sodium methylate, sodium ethylate, sodium isobutylate, potassium tert-butylate, sodium hydroxide or potassium hydroxide.

If a non-polar solvent is used, it is moreover advantageous to add a suitable phase transfer catalyst as further reaction auxiliary. Examples of such catalysts which may be mentioned are: tetrabutylammonium iodide, tetrabutylammonium bromide, tetrabutylammonium chloride, tributyl-methylphosphonium bromide, trimethyl-$C_{13}/C_{15}$-alkylammonium chloride, trimethyl-$C_{13}/C_{15}$-alkylammonium bromide, dibenzyl-dimethylammonium methylsulphate, dimethyl-$C_{12}/C_{14}$-alkyl-benzylammonium chloride, dimethyl-$C_{12}/C_{14}$-alkyl-benzylammonium bromide, tetrabutylammonium hydroxide, triethylbenzylammonium chloride, methyltrioctylammonium chloride, trimethylbenzylammonium chloride, 15-crown-5, 18-crown-6 or tris-[2-(2-methoxyethoxy)-ethyl]-amine.

The reaction temperatures in the second stage of the process according to the invention may be varied in a wide range. In general temperatures between −30° C. and +100° C. are used, preferably temperatures between −30° C. and +40° C.

To carry out the second stage of the process according to the invention, in general 1.0 to 2.0 mol, preferably 1.0 to 1.3 mol, of phenylsulphonylmethyl isocyanide of the formula (IV), 1.2 to 1.8 mol of base and optionally 0.01 to 2.0 mol, preferably 0.1 to 1.5 mol, of a phase transfer catalyst are used per mole of the acrylonitrile derivative of the formula (III).

If low-solvating solvents, such as, for example, toluene or methyl tert-butyl ether are used, one of the abovecited phase transfer catalysts must be added, and/or a polar solvent such as for example tetrahydrofuran must be admixed, which achieves the object of adjusting the reactivity of the base used and of the phenylsulphonylmethyl isocyanide of the formula (IV) so that a smooth conversion is accomplished, without having to increase the reaction temperature to the range where the danger of exothermic decomposition of the phenylsulphonylmethyl isocyanide of formula (IV) exists.

The procedure for this is such that firstly the acrylonitrile derivative of the formula (III) is placed together with the base and, if required, the phase transfer catalyst, in a suitable solvent, then the phenylsulphonylmethyl isocyanide of the formula (IV), dissolved in a suitable solvent, is added dropwise, after which the mixture is stirred for several hours at the required temperature (as a rule room temperature), precipitated phenylsulphinate is filtered off, organic solvent is removed in vacuo and the residue is treated with water, where the desired 3-substituted 4-cyano-pyrrole compounds of the formula (I) occur as precipitate, and all by-products remain in solution. Filtration and drying give products of high purity.

In a variant of the process according to the invention, it is also possible to carry out the first and the second stage in one reaction step without isolation of the acrylonitrile derivative of the formula (III), in a so-called "one-pot process" (compare in this respect also the preparation examples).

The 3-substituted 4-cyano-pyrrole compounds obtainable with the aid of the process according to the invention are known fungicides for agricultural use (compare e.g. EP 293 711 or EP 315 869 or DE-OS (German Published Specification) 37 37 984 or DE-OS (German Published Specification) 38 00 387).

PREPARATION EXAMPLES

Example 1

Variant a)

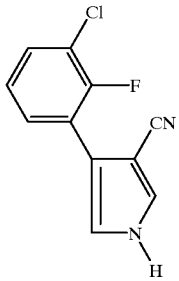

8.65 g (0.077 mol) of t-potassium butylate are placed in 100 ml of tetrahydrofuran and at −10° C. a mixture of 10 g (0.055 mol) of 2-fluoro-3-chlorocinnamonitrile and 14 g (0.071 mol) of p-toluenesulphonylmethyl isocyanide (TOSMIC) in 200 ml of tetrahydrofuran is added. After stirring for 3 hours at room temperature, the tetrahydrofuran is distilled off in vacuo, the residue is taken up in water, and the resulting precipitate is filtered off with suction and dried.

12.0 g (95% of theory) of 3-cyano-4-(2-fluoro-3-chlorophenyl)-pyrrole are obtained (content: 95%; determination by HPLC), of melting point 180° C. to 181° C.

Example 1

Variant b)

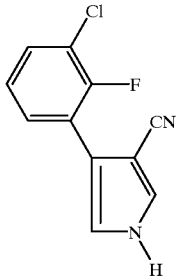

1.3 g (0.023 mol) of potassium hydroxide powder is placed in 30 ml of tetrahydrofuran, 9 ml of tris-[2-(2-methoxyethoxy)ethyl]-amine are added and at −10° C. a mixture of 3 g (0.016 mol) of 2-fluoro-3-chlorocinnamonitrile and 4.2 g (0.022 mol) of p-toluenesulphonylmethyl isocyanide (TOSMIC) in 60 ml of tetrahydrofuran is added. After stirring for 3 hours at room temperature, the tetrahydrofuran is distilled off in vacuo, the residue is taken up in water, and the resulting precipitate is filtered off with suction and dried.

2.9 g (73% of theory) of 3-cyano-4-(2-fluoro-3-chlorophenyl)-pyrrole are obtained (content 91%; determination by gas chromatography) of melting point 180° C.

Example 1

Variant c)

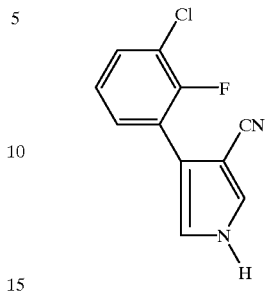

To 1.65 g (0.009 mol) of 2-fluoro-3-chlorocinnamonitrile and 2.4 g (0.01 mol) of p-chlorophenylsulphonylmethyl isocyanide in 20 ml of dimethoxyethane is added at 0° C. with stirring 1.35 g (0.015 mol) of sodium hydroxide dissolved in a little water, with stirring after addition is ended for a further hour at 0° C. For work-up, the solvent is distilled off in vacuo, the residue is taken up in water, and the resulting precipitate is filtered off with suction and dried.

1.65 g (81% of theory) of 3-cyano-4-(2-fluoro-3-chlorophenyl)-pyrrole is obtained (content 98%; determination by gas chromatography) of melting point 180° C. to 181° C.

Example 1

Variant d)

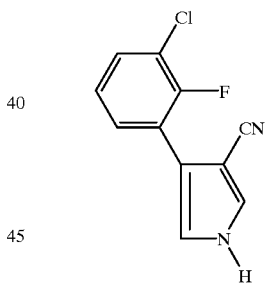

(One-Pot Process 3.0 g (0.014 mol) of 1-bromo-2-fluoro-3-chlorobenzene and 1.15 g (0.021 mol) of acrylonitrile are placed in 100 ml of dimethylformamide, 0.07 g (0.3 mmol) of palladium acetate, 3 g (0.036 mol) of sodium hydrogen carbonate and 1.7 g (0.006 mol) of tetrabutylammonium chloride are added and heated to 120° C. under a nitrogen atmosphere. After a reaction time of 16 hours the reaction mixture is suctioned off, and the filtrate together with 3.65 g (0.019 mol) of p-toluenesulphonylmethyl isocyanide (TOSMIC) is added to 2.25 g (0.020 mol) of t-potassium butylate in 20 ml of dimethylformamide. After stirring for 3 hours at room temperature the reaction mixture is added to water and the resulting precipitate is filtered off with suction and dried.

2.65 g (67% of theory) of 3-cyano-4-(2-fluoro-3-chlorophenyl)-pyrrole are obtained (content 90%; determination by gas chromatography) of melting point 178° C.

| EXAMPLE | YIELD OF THEORY | PHYSICAL CONSTANTS |
|---|---|---|
| 2) 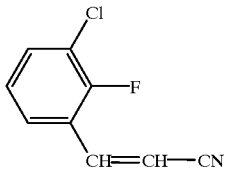 | 91% | brown oil |
| 3) 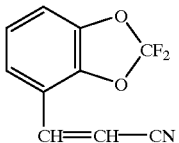 | 87% | brown oil |

Precursor Preparation

Example III-1

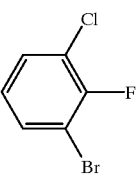

5.0 g (0.024 mol) of 1-bromo-2-fluoro-3-chlorobenzene and 1.9 g (0.036 mol) of acrylonitrile are placed in 150 ml of dimethylformamide, 0.11 g (0.5 mmol) of palladium acetate, 5 g (0.060 mol) of sodium hydrogen carbonate and 2.85 g (0.010 mol) of tetrabutylammonium chloride are added and heated to 120° C. After a reaction time of 16 hours the reaction mixture is poured into water, extracted with ethyl acetate, washed with water and 2 normal hydrochloric acid, dried and freed from the solvent in vacuo.

4.1 g (89% of theory) of 2-fluoro-3-chlorocinnamonitrile are obtained (content 99%; determination by gas chromatography) of melting point 92° C. to 94° C.

Example III-1 (Comparison Example)

(Compare in this respect J. Chem. Soc., Perkin Trans 1, 1987, 2597 and J. Organometall. Chem. 258, 101, [1983])

Example III-2

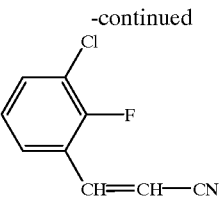

Yield: 97% of theory
brown oil

-continued

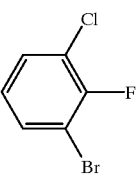

To 0.3 g (0.0014 mol) of 1-bromo-2-fluoro-3-chlorobenzene and 0.1 g (0.0018 mol) of acrylonitrile in 10 ml of triethylamine are added 0.0032 g (0.015 mmol) of palladium acetate and 0.015 g (0.058 mmol) of triphenylphosphine. After reaction for 7 hours at reflux temperature the reaction mixture is analysed by gas chromatography. The desired product (2-fluoro-3-chlorocinnamonitrile) is not found.

Example II-1

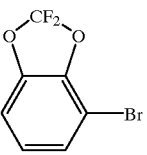

To 80 ml of a 65 % strength sulphuric acid are added at room temperature dropwise with stirring 14.6 g (0.1 mol) of 2-fluoro-3-chloroaniline, the mixture is cooled to 0° C., a solution of 11 g (0.16 mol) sodium nitrite in 30 ml of water is added dropwise, with stirring at 5° C. for 30 minutes afterwards, and then this solution is added in portions to a mixture of 45 ml of 48% strength hydrobromic acid and 2.8 g of copper(I) bromide. The reaction mixture is stirred for one hour at room temperature and then for 90 minutes at 90° C. For work-up the reaction solution is cooled, diluted with 200 ml of water, extracted three times with a total of 300 ml of methyl tert-butyl ether, washed with water, dried over sodium sulphate and freed from the solvent in vacuo.

21 g (97% of theory) of 1-bromo-3-chloro-2-fluorobenzene are obtained of melting point 43° C. and of boiling point 88° C. to 92° C. at 32 mbar.

Example II-2

To 15.8 g (0.1 mol) of 2,2-difluorobenzodioxole (compare e.g. DE-OS (German Published Specification) 19 21 741) in 80 ml of absolute tetrahydrofuran are added dropwise under a dry nitrogen atmosphere at −78° C. within 1 hour with stirring 45 ml (0,11 mol) of n-butyllithium (2.5 molar in n-hexane), and after stirring for 1 hour at −78° C. 16 g (0.1 mol) of bromine are then added dropwise with stirring at −78° C. The mixture is stirred for a further 90 minutes at −78° C. then allowed to come to room temperature, and is hydrolysed with 75 ml of 10 per cent hydrochloric acid. For work-up the organic phase is separated off, washed with 1 normal hydrochloric acid, dried over sodium sulphate, concentrated in vacuo and the residue is distilled in a water pump vacuum.
11.3 g (46% of theory) of 4-bromo-2,2-difluorobenzodioxole are obtained of boiling point 74° C. to 75° C. at 20 mbar.
What is claimed is:
1. The compound 4-bromo-2,2-difluorobenzodioxole of the formula
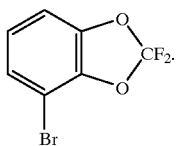
* * * * *